US011229174B2

(12) United States Patent
MacDonald et al.

(10) Patent No.: US 11,229,174 B2
(45) Date of Patent: Jan. 25, 2022

(54) **METHOD FOR ENHANCING CROP PERFORMANCE IN *BRASSICA***

(71) Applicant: BASF AGRICULTURAL SOLUTIONS SEED US LLC, Research Triangle Park, NC (US)

(72) Inventors: Robert MacDonald, Strathmore (CA); Susan Slater, Martensville (CA); Derek Lewis, Winnipeg (CA); Joel Gorman, Calgary (CA)

(73) Assignee: BASF AGRICULTURAL SOLUTIONS SEED US LLC, Research Triangle Park, NC (US)

( * ) Notice: Subject to any disclaimer, the term of this patent is extended or adjusted under 35 U.S.C. 154(b) by 40 days.

(21) Appl. No.: 15/761,770

(22) PCT Filed: Sep. 16, 2016

(86) PCT No.: PCT/EP2016/072058
§ 371 (c)(1),
(2) Date: Mar. 20, 2018

(87) PCT Pub. No.: WO2017/050663
PCT Pub. Date: Mar. 30, 2017

(65) Prior Publication Data
US 2020/0253141 A1 Aug. 13, 2020

(30) Foreign Application Priority Data

Sep. 22, 2015 (WO) ................ PCT/CA2015/050935

(51) Int. Cl.
| | |
|---|---|
| *A01G 22/00* | (2018.01) |
| *A01H 6/20* | (2018.01) |
| *A01H 1/02* | (2006.01) |
| *A01H 5/10* | (2018.01) |

(52) U.S. Cl.
CPC ............. *A01H 6/202* (2018.05); *A01G 22/00* (2018.02); *A01H 1/02* (2013.01); *A01H 5/10* (2013.01)

(58) Field of Classification Search
CPC .................................................. A01G 22/00
See application file for complete search history.

(56) References Cited

FOREIGN PATENT DOCUMENTS

| EP | 3352560 B1 | 1/2021 |
|---|---|---|
| WO | 2017050663 A1 | 3/2017 |
| WO | 2017049379 A1 | 3/2021 |

OTHER PUBLICATIONS

Elliot et al Canadian Journal of Plant Science vol. 88, No. 1, pp. 207-217 (Year: 2008).*
Green et al Pest Management Science vol. 64, pp. 332-339 (Year: 2008).*
Taryn Jaye Dickson Master of Science Dissertation Dept. of Soil Sci. University of Manitoba, Winnipeg (Year: 2014).*
Elliott, et al., "Effects of seed size and seed weight on seedling establishment, vigour and tolerance of Argentine canola (*Brassica napus*) to flea beetles, *Phyllotreta* spp.," Canadian Journal of Plant Science, (2008), vol. 88, No. 1:207-217.
Kutcher, et al., "Response of herbicide-tolerant canola (*Brassica napus* L.) cultivars to four row spacings and three seeding rates in a no-till production system," Canadian Journal of Plant Science, (2013), vol. 93, No. 6: 1229-1236.
Yang, et al., "Up to 32% yield increase with optimized spatial patterns of canola plant establishment in western Canada," Agronomy for Sustainable Development, (2014), vol. 34, No. 4: 793-801.
Harker, et al., "Seed size and seeding rate effects on canola emergence, development, yield and seed weight," Canadian Journal of Plant Science, (2015), vol. 95, No. 1:1-8.
Yong-Bo, et al., "The Effects of Seed Size on Hybrids Formed between Oilseed Rape (*Brassica napus*) and Wild Brown Mustard (*B. juncea*)", Plos One, (2012), vol. 7, No. 6: e39705.
"Canola best practice management guide for south-eastern Australia", Grains Research and Development Corporation, 2009, 92 pages.
"Feldsamenkatalog", UFA Samen-Semences, 2014, pp. 38-39.
"Guide de culture, Colza", Terres Inovia, May 2015, 40 pages.
"Letter by BASF Agricultural Solutions Seed US LLC to EPO", Jul. 11, 2019, 5 pages.
"Pflanzenschutz Hannover", Pflanzenschutz- Versuchsbericht, 2005, pp. 169-172 & 369-374.
"Registered Variety: 5440 (Canola and Rapeseed)", Canadian Food Inspection Agency, Reg. No. 6285, Apr. 30, 2007, 2 pages.
"Registered Variety: 73-75 RR (Canola and Rapeseed)", Canadian Food Inspection Agency, Reg. No. 7012, Apr. 20, 2011, 2 pages.
"Screenshot of the abstract of Tan, et al., "Imidazolinone-tolerant crops: history, current status and future", Pest Management Science, vol. 61, Issue 3, Dec. 31, 2004, pp. 246-257.", 1 page.
"UFOP- Information Winterrapsaussaat 2010", Union zur Förderung von Oel- und Proteinpflanzen E.V., 2010, pp. 1-7.
Christen, et al., "Chapter 2: Biotechnologie, Züchtung und Saatgut", Winterraps—Das Handbuch für Profis, 1st edition, Mar. 1, 2007, pp. 46-47.
Dr. S. Shirtliffe, "Determining the economic plant density in canola", Final Report, Prepared for Saskatchewan Canola Development Commission, Dec. 10, 2009, 33 pages.
F. Svaton, "Semenarska kvalita a vynos ozime repky ve vztahu k velinkosti osiva", Rostlinna Vyroba, 1993, pp. 395-400.
H. Schonberger, "Optimale Anbauintensitat bei schwankenden Preisen", Prasentation Feldtag der Saaten Union, N. U. Agrar GMBH, Jun. 24, 2011, 31 pages.

(Continued)

*Primary Examiner* — David H Kruse
(74) *Attorney, Agent, or Firm* — Arent Fox LLP

(57) ABSTRACT

The present invention relates to a method for enhancing crop performance in *Brassica*, the method comprising providing *Brassica* seeds which have been sorted so that at least 90% of the seed population have a seed diameter of at least 1.7 mm; and seeding said *Brassica* seeds at a seeding rate sufficient to establish a population of *Brassica* plants so that the plants have a density of 40 to 95 plants per m² when the plants are at any one or more of phenological growth stages 11, 12, 13, 14, or 15, according to the BBCH scale; and that the plants show an establishment rate of at least 40%.

12 Claims, No Drawings

(56) References Cited

OTHER PUBLICATIONS

Hanson, et al., "Seeding Rate, Seeding Depth, and Cultivar Influence on Spring Canola Performance in the Northern Great Plains", Agronomy Journal, vol. 100, Issue 5, Sep. 1, 2008, pp. 1339-1346.
Harper, et al., "Revised growth-stage key for Brassica Campestris and B. Napus", Canadian Journal of Plant Science, vol. 55, Issue 2, Apr. 1975, pp. 657-658.
Heather, et al., "Effect of Seed Size and Cultivar on Emergence and Stand Establishment of Broccoli in Crusted Soil", Journal of the American Society for Horticultural Science, vol. 116, Issue 6, Jan. 1, 1991, pp. 946-949.
Jugulam, et al., "Transfer of Dicamba Tolerance from Sinapis arvensis to Brassica napus via Embryo Rescue and Recurrent Backcross Breeding", PloS one, vol. 10, Issue 11, Nov. 4, 2015, 13 pages.
Klaus-Ulrich Heyland, "Spezieller Pflanzenbau", Landwirtschaftliches Lehrbuch, 7th edition, Oct. 1, 1996, p. 109-111.
Liu, et al., "The Effects of Seed Size on Hybrids Formed between Oilseed Rape (Brassica napus) and Wild Brown Mustard (B. juncea)", PloS One, vol. 7, Issue 6, Jun. 22, 2012, pp. 1-8.
Lukas Aebi, "Intensive Kontrollen Notwendig", Fachzeitschrift der fenaco-landi gruppe, UFA-REVUE, Jun. 2013, pp. 34-35.
P. Baranyk, "Vliv Kalibrace Osiva Na Nektere Vlastnosti Porostu Repky Ozime", Sbornik- System Vyroby Repky, 9th Evaluation training, Nov. 17-19, 1992, pp. 116-119.
Rahman, et al., "72P01 CL Clearfield herbicide-tolerant spring canola", Canadian Journal of Plant Science, vol. 91, Issue 3, May 2011, pp. 527-528.
Stringam, et al., "Transgenic Herbicide Tolerant Canola—The Canadian Experience", Crop Science, vol. 43, Issue 5, Sep. 1, 2003, pp. 1590-1593.
Yantai, et al., "Canola seed yield and phenological responses to plant density", Canadian Journal of Plant Science, vol. 96, Issue 1, Feb. 26, 2016, pp. 151-159.
Elliott, et al., "Effects of seed size and seed weight on seedling establishment, seedling vigour and tolerance of summer turnip rape (Brassica rapa) to flea beetles, Phyllotreta spp.", Canadian Journal of Plant Science, vol. 87, Issue 2, Apr. 2007, 385-393.
P. Baranyk, "Vývoj odrudove skladby ozime repky v CR a vliv kalibrace osiva na vyos semene", Rostlinna Vyroba, vol. 41, Issue 7, 1995, pp. 325-331.

* cited by examiner

METHOD FOR ENHANCING CROP PERFORMANCE IN *BRASSICA*

CROSS-REFERENCE TO RELATED APPLICATIONS

This application is a National Stage entry of International Application No. PCT/EP2016/072058, filed 16 Sep. 2016, which claims priority to Canadian Patent Application No. PCT/CA2015/050935, filed 22 Sep. 2015.

BACKGROUND

FIELD

This invention relates to methods for enhancing crop performance, in particular a yield increase in *Brassica* plants.

DESCRIPTION OF RELATED ART

Members of the *Brassica* genus are economically important crops in particular for oil production in many countries of the world. Examples are *Brassica napus*, in particular spring oilseed rape, or canola, or winter oilseed rape, or *Brassica juncea*. Especially in areas with challenging climatic conditions, like Canada, crop performance is not only determined by the genetics of the different varieties, but by competitive ability for resources like light, nutrients, or soil water. Therefore, agronomic practices used in cultivating *Brassica*, particularly canola, significantly influence plant performance (Yang et al, Agron. Sustain. Dev. (2014) 34: 793-801). Recent discussions indicate that in addition to the genotype of a certain variety the seed quality may have an impact on the later performance eg on yield. In order to characterize seed quality different parameters can be applied. Seed size has been discussed as a major factor influencing later performance of the crops eg growth rates (Turnbull et al, Ecology (2012), 93(6), 1283-9). Seed size can be measured in different ways, for example as the seed diameter, or as thousand kernel/seed weight (TSW). TSW is a common parameter already used in cultivation of crops having bigger seeds like soybean or corn, yet due to the small size, TSW is not yet widely used in the cultivation of *Brassica* plants. A recent publication regarding the influence of seed size states that emergence, yield or seed quality is not influenced significantly by seed size (Harker et al Can. J Plant Sci. 2015, 95: 1 - 8).

For oil seed rape, in particular Canola recommendations are typically given as seeding rate in weight/area. Using the TSW the seeding rate can be converted into No of seeded seeds/area. The current recommendation of the Canola Council is to target a plant population of 70 to 100 plants per square meter or 40-50 to 200 plants per square meter (world wide web at canolacouncil.org/canola-encyclopedia/ crop-establishment/seeding-rate/). The Canola Council recommends a wide range of seeding rates (1.12-30 kg/ha) dependent on seed survival, TSW, and plant density.

For optimal cultivation of commercial crops it is also important to achieve a certain optimal plant density. If the plant density is too low the yield potential of the field will not be optimally extracted. If the plant density is too high the plants will compete for resources with the other plants leading to potentially negative effects on yield due to stress. Too high plant densities will also promote unequal growth of the crops leading to a higher variability in the growth and maturation of the crop. This will then negatively affect the percentage of plants being harvestable at a certain point in time leaving a higher percentage of crops whose have not reached the stage of maturity (detected as the amount of chlorophyll containing seeds ("green seed") and a higher percentage of plants where seeds are lost due to lodging or pod drop. Nevertheless, various parameters, eg. agronomic practices, or seed size and seeding rate, influence crop performance. Systematic approaches determining which seed size parameters, plant densities at which crop stage and what early stage crop cultivation practices enhance crop performance are rare or ambiguous.

SUMMARY

The present invention relates to a method for enhancing crop performance in *Brassica*, the method comprising:
a. providing *Brassica* seeds which have been sorted so that at least 90% of the seed population have a seed diameter of at least 1.7 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 60%.

In another embodiment, the present invention relates to a method for enhancing crop performance in *Brassica*, said method comprising:
a. providing *Brassica* seeds which have been sorted so that at least 90% of the seed population have a seed diameter of at least 1.7 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 60%,
c. harvesting the resulting crop between BBCH stage 84 and 89 using the straight-cutting technique.

DETAILED DESCRIPTION

In one embodiment, crop species, cultivars and varieties belonging to the plant genus *Brassica* are
  *Brassica carinata*: Abyssinian mustard or Abyssinian cabbage
  *Brassica elongata*: elongated mustard
  *Brassica fruticulosa*: Mediterranean cabbage
  *Brassica juncea*: Indian mustard, brown and leaf mustards, Sarepta mustard
  *Brassica napus* comprising winter rapeseed, summer rapeseed, rutabaga (*Brassica napus* subsp *rapifera* swede/Swedish turnip/swede turnip)
  *Brassica narinosa*: broadbeaked mustard
  *Brassica nigra*: black mustard
  *Brassica oleracea* comprising cultivars like kale, cabbage, broccoli, cauliflower, kai-lan, Brussels sprouts, kohlrabi
  *Brassica perviridis*: tender green, mustard spinach
  *Brassica rapa* (syn *B. campestris*) comprising Chinese cabbage, turnip, rapini, komatsuna
  *Brassica rupestris*: brown mustard
  *Brassica septiceps*: seventop turnip
  *Brassica tournefortii*: Asian mustard
  *Brassica alba* (syn *Sinapis alba*, white mustard)

Canola Varieties

To use the name canola, an oilseed plant must meet the following internationally regulated standard: "Seeds of the genus Brassica (*Brassica napus, Brassica rapa* or *Brassica juncea*) from which the oil shall contain less than 2% erucic acid in its fatty acid profile and the solid component shall contain less than 30 micromoles of any one or any mixture of 3-butenyl glucosinolate, 4-pentenyl glucosinolate, 2-hydroxy-3 butenyl glucosinolate, and 2-hydroxy- 4-pentenyl glucosinolate per gram of air-dry, oil-free solid."

Other crop plants belonging to the plant family *Brassica* are horseradish (*Armoracia rusticana*), radish (e.g. *Raphanus sativus* var. *oleiformis, Raphanus sativus* L. var. *sativus*). Preferred *Brassica* plants are oilseed rape plants (*Brassica napus*), *Brassica rapa* and *Brassica juncea*. More preferred *Brassica* plants according to the present invention are oilseed rape plants (*Brassica napus*), more preferred winter oilseed rape plants (*Brassica napus*).

The *Brassica napus*, or *Brassica juncea* plants, or cultivars are also understood to be hybrids. Of particular interest are spring or winter oilseed rapes, especially Canola hybrids. These hybrids may have in addition new properties ("traits"), which may have been obtained by conventional biological breeding methods, such as crossing or protoplast fusion. In a further preferred embodiment, transgenic plants and plant cultivars of *Brassica* are obtained by genetic engineering, if appropriate in combination with conventional methods (Genetically Modified Organisms).

Particularly useful transgenic Brassica plants are plants containing transformation events, or a combination of transformation events, and that are listed for example in the databases for various national or regional regulatory agencies including Event BLR1 (oilseed rape, restoration of male sterility, deposited as NCIMB 41193, described in WO 2005/074671), Event MON88302 (oilseed rape, herbicide tolerance, deposited as PTA-10955, described in WO 2011/153186), Event MS11(oilseed rape, pollination control--herbicide tolerance, deposited as ATCC PTA-850 or PTA-2485, described in WO 01/031042); Event MS8 (oilseed rape, pollination control--herbicide tolerance, deposited as ATCC PTA-730, described in WO 01/041558 or US-A 2003-188347); Event RF3 (oilseed rape, pollination control--herbicide tolerance, deposited as ATCC PTA-730, described in WO 01/041558 or US-A 2003-188347); Event RT73 (oilseed rape, herbicide tolerance, not deposited, described in WO 02/036831 or US-A 2008-070260), event MON-88302-9 (oilseed rape, herbicide tolerance, ATCC Accession No. PTA-10955, WO 2011/153186A1), event DP-061061-7 (oilseed rape, herbicide tolerance, no deposit N .degree. available, WO 2012071039A1), event DP-073496-4 (oilseed rape, herbicide tolerance, no deposit number available, US2012131692).

The term "growth stage" refers to the growth stages as defined by the BBCH Codes in "Growth stages of mono- and dicotyledonous plants", 2nd edition 2001, edited by Uwe Meier from the Federal Biological Research Centre for Agriculture and Forestry. The BBCH codes are a well-established system for a uniform coding of phonologically similar growth stages of all mono- and dicotyledonous plant species. The abbreviation BBCH derives from "Biologische Bundesanstalt, Bundessortenamt and Chemische Industrie".

Some of these BBCH growth stages and BBCH codes for oilseed rape plants are indicated in the following.
Growth stage 1: Leaf development1
BBCH 10—Cotyledons completely unfolded
BBCH 11—First leaf unfolded
BBCH 12—2nd leaf unfolded
BBCH 13—3rd leaf unfolded
BBCH 14—18 Stages continuous till . . . (4-8th leaf unfolded)
BBCH 19—9 or more leaves unfolded
Growth stage 2: Formation of side shoots
BBCH 20—No side shoots
BBCH 21—Beginning of side shoot development: first side shoot detectable
BBCH 22—2nd side shoots detectable
BBCH 23—3rd side shoots detectable
BBCH 24—4th side shoots detectable
BBCH 25—5th side shoots detectable
BBCH 26-28—Stages continuous till . . . (6-8 side shoots detectable)
BBCH 29 End of side shoot development: 9 or more side shoots detectable Growth stage 3: Stem elongation2
BBCH 30—Beginning of stem elongation: no internodes ("rosette")
BBCH 31—1 visibly extended internode
BBCH 32—2nd visibly extended internode
BBCH 33—3rd visibly extended internode
BBCH 39—9 or more visibly extended internodes
Growth stage 8: Ripening
BBCH 80—Beginning of ripening: seed green, filling pod cavity
BBCH 81—10% of pods ripe, seeds dark and hard
BBCH 82—20% of pods ripe, seeds dark and hard
BBCH 83—30% of pods ripe, seeds dark and hard
BBCH 84—40% of pods ripe, seeds dark and hard
BBCH 85—50% of pods ripe, seeds dark and hard
BBCH 86—60% of pods ripe, seeds dark and hard
BBCH 87—70% of pods ripe, seeds dark and hard
BBCH 88—80% of pods ripe, seeds dark and hard
BBCH 89—Fully ripe: nearly all pods ripe, seeds dark and hard
Growth stage 9: Senescence
BBCH 97—Plant dead and dry
BBCH 99—Harvested product
BBCH 100—post harvest The seeding rate is defined as the weight of *Brassica* seeds seeded per area, eg grams/ha. The seeding rate might also be expressed as number of seeds/area, eg number of seeds per square meter. The seeding rate expressed as number of seeds per area may be converted into the seeding rate expressed as grams/ha as seed as follows: Number of seeds per square meter*TSW*10. So a seeding rate of 110 seeds per square meter of a seed lot with a TSW of 5 g corresponds to a seeding rate of 5.5 kg/ha.

The seeding rate is selected in order to achieve a certain target population of the *Brassica* plants of 40 to 95 plants/m$^2$ when the plants are at any one or more of phenological growth stages 11, 12, 13, 14, or 15, according to the BBCH scale 40 to 95 taking into account an establishment rate of at least 60%. The expression "when the plants are at any one or more of phenological growth stages 11, 12, 13, 14, or 15, according to the BBCH scale" means that the recited conditions must be met at at least of one of the specified growth stages. For example, with respect to the target population of 40 to 95 plants/m$^2$, this target population density must be achieved when the plants are in at least one (or optionally more than one) of growth stages 11, 12, 13, 14, or 15. Hence, this condition is met if e.g. the plants are at a target density of 40 to 95 plants/m$^2$ in growth stages 12 and 13, but not in growth stages 11, 14, or 15. The seeding rate is estimated based on the thousand seed weight, the establishment rate as defined below and the target population. For example a seeding rate of 5 kg/ha of a seedlot with a TSW of 4g results in seeding 125 Canola seeds per m² which would result in 75 plants/m² when the plants are at any one or more of phenological growth stages 11, 12, 13, 14, or 15, according to the BBCH scale taking into account an establishment rate of 60%. Typical seeding rates are between 2.6 to 8.0 kg per ha, between 2.6 to 6.0 kg per ha, 2.8 to 5.5 kg per ha, or 2.9 and 5.2 kg/ha.

Germination rate is defined as the percentage of seed that have germinated under optimal conditions regarding humidity and temperature as characterized by having root growth about twice the diameter of the seed. In the case of *Brassica* species, in particular spring oilseed rape, a germination test is typically performed at 20 degrees Celsius. At the time of determining the germination rate, the seedling are at any one or more of phenological growth stages 03, 04 or 05 according to the BBCH scale.

Emergence is defined as the percentage of visible seedlings at BBCH growth stages 06 to 09 based on the total number of seeds sown. Emergence can e.g. be determined by sowing canola seeds into soil at a certain depth, eg between 1.5 and 3 cm, exposing the seeds to a certain light regime, eg 16 h photoperiod with 16 degree Celsius in the light and 5 degree Celsius in the dark at a certain humidity, eg. 50 to 75% humidity and counting the number of emerged seedlings at a certain growth stage eg after one week or when the plants are at any one or more of phenological growth stages 06, 07, 08 or 09, according to the BBCH scale.

Vigour can be assessed after a prechill regime, wherein seeds are incubated in the dark at a low temperature, eg 5° C. for seven days in a suitable medium, eg potting soil/sand mixture. The samples are then incubated for a certain number of days, eg for five additional days and maintained at alternating temperatures in a certain light regime, eg 25° C. and 15° C. daily temperatures corresponding to eight hours of light and 16 hours of dark. Vigour ratings are based on the number of normal seedlings after 12 days.

Establishment is defined as the percentage of visible plants when the plants are at any one or more of phenological growth stages 11, 12, 13, 14, or 15, according to the BBCH scale based on the total number of seeds sown.

Plant density is defined as the number of plants at a certain growth stage per area unit, eg. No. of plants per square meter.

The fresh weight is the average weight of a canola seedling extending from the soil surface weighed directly after cutting the seedling above the soil surface.

The dry weight is the average weight of a canola seedling extending from the soil surface after cutting the seedling above the soil surface and drying it in an oven at 60±2 degrees Celsius for two to three days.

Seeding depth is the distance between the surface of the soil and the position of the seed in the soil at the time of seeding. The seeding depth is between 1.9 to 3.2 cm, preferably 2.0 to 3.0 cm, more preferably 2.3 to 3.0 cm.

Row spacing is the distance between the rows of sown seeds. The row spacing is between 10 to 40 cm, preferably 15 to 35 cm, more preferably 15 to 30 cm.

Straight cutting, or straight combining means the simultaneous approach of cutting the canola plants and threshing the seeds from the seed pods on the plant in contrast to swathing where the cutting process is performed first followed by a period of time where the cut plants are spread on the field and afterwards performing the threshing process. Straight cutting is usually later than BBCH stage 97.

TSW and seed size may be measured after the harvested raw seed material has been processed through a seed cleaning procedure. "Cleaning a seed" or "seed cleaning" refers to the removal of foreign material from a seed lot by sieving the mass of seeds through sieves. Foreign material to be removed from the surface of the seed includes but is not limited to fungi, bacteria, insect material, including insect eggs, larvae, and parts thereof, and any other pests that exist on the surface of the seed. The terms "cleaning a seed" or "seed cleaning" also refer to the removal of any debris or low quality, infested, or infected seeds and seeds of different species that are foreign to the sample.

Sorting of seeds according to their size, weight, shape or color can be achieved by different methods. Examples are mechanical methods by using gravity tables, indent cylinders, helix rollers or sieves with different size exclusions or optical methods using visible or infrared light or nuclear magnetic resonance for an automatic analysis of the seed followed by the sorting step.

Seed size is defined as the diameter of the seed in mm as *Brassica* seeds are essentially spherical. Seed size is measured on samples using a conventional seed counting apparatus (Seed Counter Elmor C1 by Elmor Ltd., Switzerland) or is measured by using sieves (US Standard test sieves from Fisher Scientific). Seed size determination is replicated fivefold in order to increase statistical significance. In the case of *Brassica* species, in particular spring oilseed rape, the seeds have been sorted so that 95% of a seed lot have a seed size of at least 1.7 mm, preferably at least 1.8 mm, more preferably 1.9 mm and most preferably at least 2.0 mm. In another embodiment in the case of *Brassica* species, in particular spring oilseed rape, the seeds have been sorted so that 95% of a seed lot have a seed size of at least 1.65 mm.

A seed lot describes a certain amount of seeds, including but not limited to commercial entity of seeds like a seed bag or an amount of seeds harvested at the same location.

Thousand seed weight (TSW) is defined to be the weight of 1000 seeds in grams. TSW is measured on samples using a conventional seed counting apparatus (Seed Counter Elmor C1 by Elmor Ltd., Switzerland). As the Elmor C1 does allow to measure the seed weight and therefore allow also to determine the TSW and seed size in parallel, seed size and TSW of a certain seed lot can be correlated.

In the case of *Brassica* species, in particular spring oilseed rape, the seeds have been sorted so that small seeds have a TSW of less than 3.0 g, preferably of less than 3.25 g, more preferably less than 3.5 g, even more preferably of less than 3.75 g.

In one embodiment, a method for enhancing crop performance in *Brassica* is described, wherein the seed population has a TSW of more than 3.5 g, more preferably of 3.75 g, even more preferably of more than 4.0 g.

In the case of *Brassica* species, in particular spring oilseed rape, the seeds have been sorted so that large seeds have a TSW of at least 5.5 g, preferably 5.75 g, even more preferably of 6.0 g.

*Brassica* seeds are typically seeded using the standard planter types like vaccum planters.

Crop performance is defined as the productivity of a crop planted, grown and harvested in a certain location.

One example for crop performance is yield, which is the amount of harvested material of the planted crop, eg. the seeds of a *Brassica* crop, in particular of Canola.

Yield is defined as the amount of harvested material, eg. seeds per area unit in tons/ha. Yield is also known to be positively correlated to early biomass gain as it can be defined by the final emergence rate, the fresh weight, the dry weight, the average shoot length after 14 days of growth (where the plants would be at any one or more of the BBCH stages 11, 12 or 13). Yield can also be expressed as Relative Yield Increase which is defined as the amount of harvested crop per seeded area unit compared to the amount of harvested crop per seeded area unit using an unbiased seed lot or a small seed lot. It can be provided in kilograms/hectare or bushels per acre. An unbiased seed lot comprises at least 5% seeds having a seed diameter of less than 1.7 mm. A small seed lot comprises at least 90% seeds having a seed diameter of less than 1.7 mm.

The Relative Yield Increase would be at least 103%, preferably 105%, more preferably 107.5% and most preferably 110%.

Another example for crop performance is a decrease in variability of the crop performance indicator, eg. in yield or relative yield increase, final emergence rate, the fresh weight, the dry weight, the average shoot length after 14 days of growth (when the plants are in any one or more of the BBCH stages 11, 12 or 13). The decrease in variability is observable as a lower value in the statistical parameters used for describing variability such as standard error, standard deviation, variance, range, interquartile range. The decrease in variability can also be described in qualitative terms, eg. a more uniform establishment of the crop, a more uniform development of the crop.

Another example for crop performance is while obtaining the same yield a lowering of necessary investments in growing the crop. Examples for that include lower seeding rates thereby lowering seed input investments.

In one embodiment, a method for enhancing crop performance in *Brassica* is described, said method comprising:
a. providing *Brassica* seeds which have been sorted so that at least 90% of the seed population have a seed diameter of at least 1.7 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 40%.

In one embodiment a method for enhancing crop performance in *Brassica* is described, said method comprising:
a. providing *Brassica* seeds which have been sorted so that at least 90% of the seed population have a seed diameter of at least 1.8 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 40%.

In one embodiment, a method for enhancing crop performance in *Brassica* is described, said method comprising:
a. providing *Brassica* seeds which have been sorted so that at least 90% of the seed population have a seed diameter of at least 1.9 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 40%.

In one embodiment, a method for enhancing crop performance in *Brassica* is described, said method comprising:
a. providing *Brassica* seeds which have been sorted so that at least 90% of the seed population have a seed diameter of at least 2.0 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 40%.

In one embodiment, a method for enhancing crop performance in *Brassica* is described, said method comprising:
a. providing *Brassica* seeds which have been sorted so that at least 95% of the seed population have a seed diameter of at least 1.7 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 40%.

In one embodiment a method for enhancing crop performance in *Brassica* is described, said method comprising:
a. providing *Brassica* seeds which have been sorted so that at least 95% of the seed population have a seed diameter of at least 1.8 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 40%.

In one embodiment, a method for enhancing crop performance in *Brassica* is described, said method comprising:
a. providing *Brassica* seeds which have been sorted so that at least 95% of the seed population have a seed diameter of at least 1.9 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 40%.

In one embodiment, a method for enhancing crop performance in *Brassica* is described, said method comprising:
a. providing *Brassica* seeds which have been sorted so that at least 95% of the seed population have a seed diameter of at least 2.0 mm; and
b. seeding said *Brassica* seeds at a seeding rate sufficient to establish a population of *Brassica* plants having the following characteristics:
  1) a density of 40 to 95 plants per $m^2$ when the plants are at any one or more of phenological growth stages 11, 12, 13, 14, or 15, according to the BBCH scale; and
  2) an establishment rate of at least 40%.

In one embodiment, a method for enhancing crop performance in *Brassica* is described, said method comprising:
a. providing *Brassica* seeds which have been sorted so that at least 90% of the seed population have a seed diameter of at least 1.7 mm; and
b. seeding said *Brassica* seeds at a seeding rate sufficient to establish a population of *Brassica* plants having the following characteristics:

1) a density of 40 to 95 plants per m² when the plants are at any one or more of phenological growth stages 11, 12, 13, 14, or 15, according to the BBCH scale; and
2) an establishment rate of at least 50%.

In one embodiment a method for enhancing crop performance in *Brassica* is described, said method comprising:
a. providing *Brassica* seeds which have been sorted so that at least 90% of the seed population have a seed diameter of at least 1.8 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

In one embodiment, a method for enhancing crop performance in *Brassica* is described, said method comprising:
a. providing *Brassica* seeds which have been sorted so that at least 90% of the seed population have a seed diameter of at least 1.9 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

In one embodiment, a method for enhancing crop performance in *Brassica* is described, said method comprising:
a. providing *Brassica* seeds which have been sorted so that at least 90% of the seed population have a seed diameter of at least 2.0 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

In one embodiment, a method for enhancing crop performance in *Brassica* is described, said method comprising:
a. providing *Brassica* seeds which have been sorted so that at least 95% of the seed population have a seed diameter of at least 1.7 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

In one embodiment a method for enhancing crop performance in *Brassica* is described, said method comprising:
a. providing *Brassica* seeds which have been sorted so that at least 95% of the seed population have a seed diameter of at least 1.8 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

In one embodiment, a method for enhancing crop performance in *Brassica* is described, said method comprising:
a. providing *Brassica* seeds which have been sorted so that at least 95% of the seed population have a seed diameter of at least 1.9 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

In one embodiment, a method for enhancing crop performance in *Brassica* is described, said method comprising:
a. providing *Brassica* seeds which have been sorted so that at least 95% of the seed population have a seed diameter of at least 2.0 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

In one embodiment, a method for enhancing crop performance in *Brassica* is described, said method comprising:
a. providing *Brassica* seeds which have been sorted so that at least 90% of the seed population have a seed diameter of at least 1.7 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 60%.

In one embodiment a method for enhancing crop performance in *Brassica* is described, said method comprising:
a. providing *Brassica* seeds which have been sorted so that at least 90% of the seed population have a seed diameter of at least 1.8 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 60%.

In one embodiment, a method for enhancing crop performance in *Brassica* is described, said method comprising:
a. providing *Brassica* seeds which have been sorted so that at least 90% of the seed population have a seed diameter of at least 1.9 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 60%.

In one embodiment, a method for enhancing crop performance in *Brassica* is described, said method comprising:
a. providing *Brassica* seeds which have been sorted so that at least 90% of the seed population have a seed diameter of at least 2.0 mm; and
b. seeding said *Brassica* seeds at a seeding rate sufficient to establish a population of *Brassica* plants having the following characteristics:

1) a density of 40 to 95 plants per m² when the plants are at any one or more of phenological growth stages 11, 12, 13, 14, or 15, according to the BBCH scale; and
2) an establishment rate of at least 60%.

In one embodiment, a method for enhancing crop performance in *Brassica* is described, said method comprising:
a. providing *Brassica* seeds which have been sorted so that at least 95% of the seed population have a seed diameter of at least 1.7 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 60%.

In one embodiment a method for enhancing crop performance in *Brassica* is described, said method comprising:
a. providing *Brassica* seeds which have been sorted so that at least 95% of the seed population have a seed diameter of at least 1.8 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 60%.

In one embodiment, a method for enhancing crop performance in *Brassica* is described, said method comprising:
a. providing *Brassica* seeds which have been sorted so that at least 95% of the seed population have a seed diameter of at least 1.9 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 60%.

In one embodiment, a method for enhancing crop performance in *Brassica* is described, said method comprising:
a. providing *Brassica* seeds which have been sorted so that at least 95% of the seed population have a seed diameter of at least 2.0 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 60%.

In one embodiment, a method for enhancing crop performance in *Brassica* is described, said method comprising:
a. providing *Brassica* seeds which have been sorted so that at least 90% of the seed population have a seed diameter of at least 1.7 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 70%.

In one embodiment a method for enhancing crop performance in *Brassica* is described, said method comprising:

a. providing *Brassica* seeds which have been sorted so that at least 90% of the seed population have a seed diameter of at least 1.8 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 70%.

In one embodiment, a method for enhancing crop performance in *Brassica* is described, said method comprising:
a. providing *Brassica* seeds which have been sorted so that at least 90% of the seed population have a seed diameter of at least 1.9 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 70%.

In one embodiment, a method for enhancing crop performance in *Brassica* is described, said method comprising:
a. providing *Brassica* seeds which have been sorted so that at least 90% of the seed population have a seed diameter of at least 2.0 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 70%.

In one embodiment, a method for enhancing crop performance in *Brassica* is described, said method comprising:
a. providing *Brassica* seeds which have been sorted so that at least 95% of the seed population have a seed diameter of at least 1.7 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 70%.

In one embodiment a method for enhancing crop performance in *Brassica* is described, said method comprising:
a. providing *Brassica* seeds which have been sorted so that at least 95% of the seed population have a seed diameter of at least 1.8 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 70%.

In one embodiment, a method for enhancing crop performance in *Brassica* is described, said method comprising:
a. providing *Brassica* seeds which have been sorted so that at least 95% of the seed population have a seed diameter of at least 1.9 mm; and
b. seeding said *Brassica* seeds at a seeding rate sufficient to establish a population of *Brassica* plants having the following characteristics:

1) a density of 40 to 95 plants per m² when the plants are at any one or more of phenological growth stages 11, 12, 13, 14, or 15, according to the BBCH scale; and
2) an establishment rate of at least 70%.

In one embodiment, a method for enhancing crop performance in *Brassica* is described, said method comprising:
a. providing *Brassica* seeds which have been sorted so that at least 95% of the seed population have a seed diameter of at least 2.0 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 70%.

In one embodiment, a method for enhancing crop performance in *Brassica* is described, said method comprising:
a. providing *Brassica* seeds which have been sorted so that at least 90% of the seed population have a seed diameter of at least 1.7 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 80%.

In one embodiment a method for enhancing crop performance in *Brassica* is described, said method comprising:
a. providing *Brassica* seeds which have been sorted so that at least 90% of the seed population have a seed diameter of at least 1.8 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 80%.

In one embodiment, a method for enhancing crop performance in *Brassica* is described, said method comprising:
a. providing *Brassica* seeds which have been sorted so that at least 90% of the seed population have a seed diameter of at least 1.9 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 80%.

In one embodiment, a method for enhancing crop performance in *Brassica* is described, said method comprising:
a. providing *Brassica* seeds which have been sorted so that at least 90% of the seed population have a seed diameter of at least 2.0 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 80%.

In one embodiment, a method for enhancing crop performance in *Brassica* is described, said method comprising:
a. providing *Brassica* seeds which have been sorted so that at least 95% of the seed population have a seed diameter of at least 1.7 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 80%.

In one embodiment a method for enhancing crop performance in *Brassica* is described, said method comprising:
a. providing *Brassica* seeds which have been sorted so that at least 95% of the seed population have a seed diameter of at least 1.8 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 80%.

In one embodiment, a method for enhancing crop performance in *Brassica* is described, said method comprising:
a. providing *Brassica* seeds which have been sorted so that at least 95% of the seed population have a seed diameter of at least 1.9 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 80%.

In one embodiment, a method for enhancing crop performance in *Brassica* is described, said method comprising:
a. providing *Brassica* seeds which have been sorted so that at least 95% of the seed population have a seed diameter of at least 2.0 mm; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 80%.

In one embodiment, a method for enhancing crop performance in *Brassica* is described, said method comprising:
a. providing *Brassica* seeds which have been sorted so that the seed population has a TSW of more than 3.5 g, preferably 3.75 g; and
b. seeding said *Brassica* seeds at a seeding rate sufficient to establish a population of *Brassica* plants having the following characteristics:
1) a density of 40 to 95 plants per m² when the plants are at any one or more of phenological growth stages 11, 12, 13, 14, or 15, according to the BBCH scale; and
2) an establishment rate of at least 60%.

In one embodiment, a method for enhancing crop performance in *Brassica* is described, said method comprising:
a. providing *Brassica* seeds which have been sorted so that the seed population has a TSW of more than 3.5 g, preferably 3.75 g; and
b. seeding said *Brassica* seeds at a seeding rate sufficient to establish a population of *Brassica* plants having the following characteristics:

1) a density of 40 to 95 plants per m² when the plants are at any one or more of phenological growth stages 11, 12, 13, 14, or 15, according to the BBCH scale; and
2) an establishment rate of at least 70%.

In one embodiment, a method for enhancing crop performance in *Brassica* is described, said method comprising:
a. providing *Brassica* seeds which have been sorted so that the seed population has a TSW of more than 3.5 g, preferably 3.75 g; and
b. seeding said *Brassica* seeds at a seeding rate sufficient to establish a population of *Brassica* plants having the following characteristics:
   1) a density of 40 to 95 plants per m² when the plants are at any one or more of phenological growth stages 11, 12, 13, 14, or 15, according to the BBCH scale; and
   2) an establishment rate of at least 80%.

In one embodiment a method for enhancing crop performance in *Brassica* is described wherein the target population of the *Brassica* plants is 40 to 95 plants/m².

In one embodiment a method for enhancing crop performance in *Brassica* is described wherein the target population of the *Brassica* plants is 55 to 75 plants/m².

In one embodiment a method for enhancing crop performance in *Brassica* is described wherein the target population of the *Brassica* plants is 45 to 75 plants/m².

In one embodiment a method for enhancing crop performance in *Brassica* is described wherein the target population of the *Brassica* plants is 60 to 80 plants/m².

In one embodiment a method for enhancing crop performance in *Brassica* is described wherein the target population of the *Brassica* plants is 60 to 95 plants/m².

In one embodiment a method for enhancing crop performance in *Brassica* is described wherein the target population of the *Brassica* plants is 65 to 80 plants/m².

In one embodiment a method for enhancing crop performance in *Brassica* is described wherein the target population of the *Brassica* plants is 65 to 95 plants/m².

In one embodiment a method for enhancing crop performance in *Brassica* is described wherein the target population of the *Brassica* plants is 40 to 50 plants/m².

In one embodiment a method for enhancing crop performance in *Brassica* is described wherein the target population of the *Brassica* plants is 50 to 70 plants/m².

In one embodiment a method for enhancing crop performance in *Brassica* is described wherein the target population of the *Brassica* plants is 50 to 80 plants/m².

In one embodiment a method for enhancing crop performance in *Brassica* is described wherein the target population of the *Brassica* plants is 50 to 95 plants/m².

In one embodiment a method for enhancing crop performance in *Brassica* is described wherein the target population of the *Brassica* plants is 40 to 95 plants/m² when the plants are at any one or more of phenological growth stages 11, 12, 13, 14, or 15, according to the BBCH scale.

In one embodiment a method for enhancing crop performance in *Brassica* is described wherein the target population of the *Brassica* plants is 55 to 75 plants/m² when the plants are at any one or more of phenological growth stages 11, 12, 13, 14, or 15, according to the BBCH scale.

In one embodiment a method for enhancing crop performance in *Brassica* is described wherein the target population of the *Brassica* plants is 45 to 75 plants/m² when the plants are at any one or more of phenological growth stages 11, 12, 13, 14, or 15, according to the BBCH scale.

In one embodiment a method for enhancing crop performance in *Brassica* is described wherein the target population of the *Brassica* plants is 60 to 80 when the plants are at any one or more of phenological growth stages 11, 12, 13, 14, or 15, according to the BBCH scale.

In one embodiment a method for enhancing crop performance in *Brassica* is described wherein the target population of the *Brassica* plants is 60 to 95 when the plants are at any one or more of phenological growth stages 11, 12, 13, 14, or 15, according to the BBCH scale.

In one embodiment a method for enhancing crop performance in *Brassica* is described wherein the target population of the *Brassica* plants is 65 to 80 plants/m² when the plants are at any one or more of phenological growth stages 11, 12, 13, 14, or 15, according to the BBCH scale.

In one embodiment a method for enhancing crop performance in *Brassica* is described wherein the target population of the *Brassica* plants is 65 to 95 plants/m² when the plants are at any one or more of phenological growth stages 11, 12, 13, 14, or 15, according to the BBCH scale.

In one embodiment a method for enhancing crop performance in *Brassica* is described wherein the target population of the *Brassica* plants is 40 to 50 plants/m² when the plants are at any one or more of phenological growth stages 11, 12, 13, 14, or 15, according to the BBCH scale.

In one embodiment a method for enhancing crop performance in *Brassica* is described wherein the target population of the *Brassica* plants is 50 to 70 plants/m² when the plants are at any one or more of phenological growth stages 11, 12, 13, 14, or 15, according to the BBCH scale.

In one embodiment a method for enhancing crop performance in *Brassica* is described wherein the target population of the *Brassica* plants is 50 to 80 plants/m² when the plants are at any one or more of phenological growth stages 11, 12, 13, 14, or 15, according to the BBCH scale.

In one embodiment a method for enhancing crop performance in *Brassica* is described wherein the target population of the *Brassica* plants is 50 to 95 plants/m² when the plants are at any one or more of phenological growth stages 11, 12, 13, 14, or 15, according to the BBCH scale.

In one embodiment a method for enhancing crop performance in *Brassica* is described wherein the target population of the *Brassica* plants is 40 to 95 plants/m² when the plants are at any one or more of phenological growth stages 12, 13, 14, or 15, according to the BBCH scale.

In one embodiment a method for enhancing crop performance in *Brassica* is described wherein the target population of the *Brassica* plants is 55 to 75 plants/m² when the plants are at any one or more of phenological growth stages 12, 13, 14, or 15, according to the BBCH scale.

In one embodiment a method for enhancing crop performance in *Brassica* is described wherein the target population of the *Brassica* plants is 45 to 75 plants/m² when the plants are at any one or more of phenological growth stages 12, 13, 14, or 15, according to the BBCH scale.

In one embodiment a method for enhancing crop performance in *Brassica* is described wherein the target population of the *Brassica* plants is 60 to 80 plants/m² when the plants are at any one or more of phenological growth stages 12, 13, 14, or 15, according to the BBCH scale.

In one embodiment a method for enhancing crop performance in *Brassica* is described wherein the target population of the *Brassica* plants is 60 to 95 plants/m² when the plants are at any one or more of phenological growth stages 12, 13, 14, or 15, according to the BBCH scale.

In one embodiment a method for enhancing crop performance in *Brassica* is described wherein the target population of the *Brassica* plants is 65 to 80 plants/m² when the plants are at any one or more of phenological growth stages 12, 13, 14, or 15, according to the BBCH scale.

In one embodiment a method for enhancing crop performance in *Brassica* is described wherein the target population of the *Brassica* plants is 65 to 95 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 40 to 95 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 55 to 75 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 45 to 75 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 60 to 80 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 60 to 95 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 65 to 80 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 65 to 95 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 40 to 50 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 50 to 70 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 50 to 80 plants/m$^2$ when the plants are at any one or more of phenological growth stages 12, 13, 14, or 15, according to the BBCH scale.

In one embodiment a method for enhancing crop performance in *Brassica* is described wherein the target population of the *Brassica* plants is 50 to 95 plants/m$^2$ when the plants are at any one or more of phenological growth stages 12, 13, 14, or 15, according to the BBCH scale.

In one embodiment the *Brassica* is *Brassica napus*.

In one embodiment the *Brassica* is spring oilseed rape.

In one embodiment the *Brassica* is canola.

In one embodiment the *Brassica* is a Canola hybrid.

In one embodiment the *Brassica* is a Canola hybrid which is resistant to the herbicide Glyphosate.

In one embodiment the *Brassica* is a Canola hybrid which is resistant to the herbicide Glufosinate.

In one embodiment the *Brassica* is a Canola hybrid which is resistant to herbicides inhibiting acetolactate synthase.

In one embodiment the *Brassica* is a Canola hybrid which is resistant to herbicides inhibiting acetolactate synthase selected from the group of sulfonylureas.

In one embodiment the *Brassica* is a Canola hybrid which is resistant to herbicides inhibiting acetolactate synthase selected from the group of imidazolinones.

In one embodiment the *Brassica* is a Canola hybrid which is resistant to herbicides inhibiting acetolactate synthase selected from the group of pyrimidines.

In one embodiment the *Brassica* is a Canola hybrid which is resistant to the herbicide 2,4-Dichlorophenoxyacetic acid (2,4-D).

In one embodiment the *Brassica* is a Canola hybrid which is resistant to the herbicide 3,6-dichloro-2-methoxybenzoic acid (Dicamba).

In one embodiment the *Brassica* is a Canola hybrid selected from the group consisting of Invigor L140P (Bayer CropScience), L160S (Bayer CropScience), L252 (Bayer CropScience), L261 (Bayer CropScience), L120 (Bayer CropScience), L130 (Bayer CropScience), L135C (Bayer CropScience), 5440 (Bayer CropScience), L156H (Bayer CropScience), L150 (Bayer CropScience), L154 (Bayer CropScience), L159 (Bayer CropScience), 45H31 (Pioneer), 43E01 (Pioneer), 43E02 (Pioneer), 43E03 (Pioneer), 45S56 (Pioneer), 45S54 (Pioneer), 45S52 (Pioneer), 45S53 (Pioneer), 45H33 (Pioneer), 45H29 (Pioneer), 45H76 (Pioneer), 46H75 (Pioneer), 75-65 RR (Monsanto), 74-54 RR (Monsanto), 74-44 RR (Monsanto), 73-75 RR (Monsanto), 73-45 RR (Monsanto), 73-15 RR (Monsanto).

In one embodiment the seeds are treated before seeding with at least one active ingredient selected from the group consisting of prothioconazole, tebuconazole, propiconazole, metconazole, boscalid, fluopyram, fluxapyroxad, benzovindiflupyr, sedaxane, bixafen, penflufen, azoxystrobin, trifloxystrobin, fluoxastrobin, metominostrobin, metalaxyl, metalaxyl-M, broflanilide, chlorantraniliprole, cyantraniliprole, cyclaniliprole, cyhalodiamide, flubendiamide, tetraniliprole spirotetramat, spiromesifen, imidacloprid, thiamethoxam, clothianidin, sulfoxaflor.

A method for enhancing crop performance in *Brassica napus* is described, said method comprising:

a. providing *Brassica napus* seeds which have been sorted so that at least 90% of the seed population have a seed diameter of at least 1.7 mm; and b. seeding said *Brassica napus* seeds at a seeding rate sufficient to establish a population of *Brassica napus* plants having the following characteristics:

1) a density of 40 to 95 plants per m$^2$ when the plants are at any one or more of phenological growth stages 11, 12, 13, 14, or 15, according to the BBCH scale; and 2) an establishment rate of at least 40%.

A method for enhancing crop performance in *Brassica napus* is described, said method comprising:

a. providing *Brassica napus* seeds which have been sorted so that at least 95% of the seed population have a seed diameter of at least 1.7 mm; and b. seeding said *Brassica napus* seeds at a seeding rate sufficient to establish a population of *Brassica napus* plants having the following characteristics:

1) a density of 40 to 95 plants per m$^2$ when the plants are at any one or more of phenological growth stages 11, 12, 13, 14, or 15, according to the BBCH scale; and 2) an establishment rate of at least 40%.

A method for enhancing crop performance in *Brassica napus* is described, said method comprising:
a. providing *Brassica napus* seeds which have been sorted so that at least 90% of the seed population have a seed diameter of at least 1.7 mm; and
b. seeding said *Brassica napus* seeds at a seeding depth of 1.9 to 3.2 cm and at a seeding rate sufficient to establish a population of *Brassica napus* plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%.

A method for enhancing crop performance in *Brassica napus* is described, said method comprising:
a. providing *Brassica napus* seeds which have been sorted so that at least 95% of the seed population have a seed diameter of at least 1.7 mm; and
b. seeding said *Brassica napus* seeds at a seeding depth of 1.9 to 3.2 cm and at a seeding rate sufficient to establish a population of *Brassica napus* plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%.

A method for enhancing crop performance in *Brassica napus*, said method comprising:
a. providing *Brassica napus* seeds which have been sorted so that at least 95% of the seed population have a seed diameter of at least 1.7 mm; and
b. seeding said *Brassica napus* seeds at a seeding depth of 1.9 to 3.2 cm and at a seeding rate sufficient to establish a population of *Brassica napus* plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%,
   3) harvesting the resulting crop between BBCH stage 84 and 89 using the straight-cutting technique.

A method for enhancing crop performance in a Canola hybrid is described, said method comprising:
a. providing Canola hybrid seeds which have been sorted so that at least 90% of the seed population have a seed diameter of at least 1.7 mm; and
b. seeding said Canola hybrid seeds at a seeding rate sufficient to establish a population of Canola hybrid plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%.

A method for enhancing crop performance in a Canola hybrid is described, said method comprising:
a. providing Canola hybrid seeds which have been sorted so that at least 95% of the seed population have a seed diameter of at least 1.7 mm; and
b. seeding said Canola hybrid seeds at a seeding rate sufficient to establish a population of Canola hybrid plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%.

A method for enhancing crop performance in a Canola hybrid is described, said method comprising:
a. providing Canola hybrid seeds which have been sorted so that at least 90% of the seed population have a seed diameter of at least 1.7 mm; and
b. seeding said Canola hybrid seeds at a seeding depth of 1.9 to 3.2 cm and at a seeding rate sufficient to establish a population of Canola hybrid plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%.

A method for enhancing crop performance in a Canola hybrid is described, said method comprising:
a. providing Canola hybrid seeds which have been sorted so that at least 95% of the seed population have a seed diameter of at least 1.7 mm; and
b. seeding said Canola hybrid seeds at a seeding depth of 1.9 to 3.2 cm and at a seeding rate sufficient to establish a population of Canola hybrid plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%.

A method for enhancing crop performance in a Canola hybrid, said method comprising:
a. providing Canola hybrid seeds which have been sorted so that at least 95% of the seed population have a seed diameter of at least 1.7 mm; and
b. seeding said Canola hybrid seeds at a seeding depth of 1.9 to 3.2 cm and at a seeding rate sufficient to establish a population of Canola hybrid plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%,
   3) harvesting the resulting crop between BBCH stage 84 and 89 using the straight-cutting technique.

A method for enhancing crop performance in *Brassica napus* is described, said method comprising:
a. providing *Brassica napus* seeds which have been sorted so that the seed population has a TSW of more than 3.5 g, preferably 3.75 g; and
b. seeding said *Brassica napus* seeds at a seeding rate sufficient to establish a population of *Brassica napus* plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%.

A method for enhancing crop performance in *Brassica napus* is described, said method comprising:
a. providing *Brassica napus* seeds which have been sorted so that the seed population has a TSW of more than 3.5 g, preferably 3.75 g; and
b. seeding said *Brassica napus* seeds at a seeding depth of 1.9 to 3.2 cm and at a seeding rate sufficient to establish a population of *Brassica napus* plants having the following characteristics:
   1) a density of 40 to 95 plants per $m^2$ when the plants are at any one or more of phenological growth stages 11, 12, 13, 14, or 15, according to the BBCH scale; and
   2) an establishment rate of at least 40%.

A method for enhancing crop performance in *Brassica napus*, said method comprising:
a. providing *Brassica napus* seeds which have been sorted so that the seed population has a TSW of more than 3.5 g, preferably 3.75 g; and
b. seeding said *Brassica napus* seeds at a seeding depth of 1.9 to 3.2 cm and at a seeding rate sufficient to establish a population of *Brassica napus* plants having the following characteristics:
  1) a density of 40 to 95 plants per m² when the plants are at any one or more of phenological growth stages 11, 12, 13, 14, or 15, according to the BBCH scale; and
  2) an establishment rate of at least 40%,
  3) harvesting the resulting crop between BBCH stage 84 and 89 using the straight-cutting technique.

A method for enhancing crop performance in a Canola hybrid is described, said method comprising:
a. providing Canola hybrid seeds which have been sorted so that the seed population has a TSW of more than 3.5 g, preferably 3.75 g; and
b. seeding said Canola hybrid seeds at a seeding rate sufficient to establish a population of Canola hybrid plants having the following characteristics:
  1) a density of 40 to 95 plants per m² when the plants are at any one or more of phenological growth stages 11, 12, 13, 14, or 15, according to the BBCH scale; and
  2) an establishment rate of at least 40%.

A method for enhancing crop performance in a Canola hybrid is described, said method comprising:
a. providing Canola hybrid seeds which have been sorted so that the seed population has a TSW of more than 3.5 g, preferably 3.75 g; and
b. seeding said Canola hybrid seeds at a seeding depth of 1.9 to 3.2 cm and at a seeding rate sufficient to establish a population of Canola hybrid plants having the following characteristics:
  1) a density of 40 to 95 plants per m² when the plants are at any one or more of phenological growth stages 11, 12, 13, 14, or 15, according to the BBCH scale; and
  2) an establishment rate of at least 40%.

A method for enhancing crop performance in a Canola hybrid, said method comprising:
a. providing Canola hybrid seeds which have been sorted so that the seed population has a TSW of more than 3.5 g, preferably 3.75 g; and
b. seeding said Canola hybrid seeds at a seeding depth of 1.9 to 3.2 cm and at a seeding rate sufficient to establish a population of Canola hybrid plants having the following characteristics:
  1) a density of 40 to 95 plants per m² when the plants are at any one or more of phenological growth stages 11, 12, 13, 14, or 15, according to the BBCH scale; and
  2) an establishment rate of at least 40%,
  3) harvesting the resulting crop between BBCH stage 84 and 89 using the straight-cutting technique.

A method for enhancing crop performance in *Brassica napus* is described, said method comprising:
a. providing *Brassica napus* seeds which have been sorted so that at least 90% of the seed population have a seed diameter of at least 1.7 mm; and
b. seeding said *Brassica napus* seeds at a seeding rate sufficient to establish a population of *Brassica napus* plants having the following characteristics:
  1) a density of 40 to 95 plants per m² when the plants are at any one or more of phenological growth stages 11, 12, 13, 14, or 15, according to the BBCH scale; and
  2) an establishment rate of at least 50%.

A method for enhancing crop performance in *Brassica napus* is described, said method comprising:
a. providing *Brassica napus* seeds which have been sorted so that at least 95% of the seed population have a seed diameter of at least 1.7 mm; and
b. seeding said *Brassica napus* seeds at a seeding rate sufficient to establish a population of *Brassica napus* plants having the following characteristics:
  1) a density of 40 to 95 plants per m² when the plants are at any one or more of phenological growth stages 11, 12, 13, 14, or 15, according to the BBCH scale; and
  2) an establishment rate of at least 50%.

A method for enhancing crop performance in *Brassica napus* is described, said method comprising:
a. providing *Brassica napus* seeds which have been sorted so that at least 90% of the seed population have a seed diameter of at least 1.7 mm; and
b. seeding said *Brassica napus* seeds at a seeding depth of 1.9 to 3.2 cm and at a seeding rate sufficient to establish a population of *Brassica napus* plants having the following characteristics:
  1) a density of 40 to 95 plants per m² when the plants are at any one or more of phenological growth stages 11, 12, 13, 14, or 15, according to the BBCH scale; and
  2) an establishment rate of at least 50%.

A method for enhancing crop performance in *Brassica napus* is described, said method comprising:
a. providing *Brassica napus* seeds which have been sorted so that at least 95% of the seed population have a seed diameter of at least 1.7 mm; and
b. seeding said *Brassica napus* seeds at a seeding depth of 1.9 to 3.2 cm and at a seeding rate sufficient to establish a population of *Brassica napus* plants having the following characteristics:
  1) a density of 40 to 95 plants per m² when the plants are at any one or more of phenological growth stages 11, 12, 13, 14, or 15, according to the BBCH scale; and
  2) an establishment rate of at least 50%.

A method for enhancing crop performance in *Brassica napus*, said method comprising:
a. providing *Brassica napus* seeds which have been sorted so that at least 95% of the seed population have a seed diameter of at least 1.7 mm; and
b. seeding said *Brassica napus* seeds at a seeding depth of 1.9 to 3.2 cm and at a seeding rate sufficient to establish a population of *Brassica napus* plants having the following characteristics:
  1) a density of 40 to 95 plants per m² when the plants are at any one or more of phenological growth stages 11, 12, 13, 14, or 15, according to the BBCH scale; and
  2) an establishment rate of at least 50%,
  3) harvesting the resulting crop between BBCH stage 84 and 89 using the straight-cutting technique.

A method for enhancing crop performance in a Canola hybrid is described, said method comprising:
a. providing Canola hybrid seeds which have been sorted so that at least 90% of the seed population have a seed diameter of at least 1.7 mm; and
b. seeding said Canola hybrid seeds at a seeding rate sufficient to establish a population of Canola hybrid plants having the following characteristics:
  1) a density of 40 to 95 plants per m² when the plants are at any one or more of phenological growth stages 11, 12, 13, 14, or 15, according to the BBCH scale; and
  2) an establishment rate of at least 50%.

A method for enhancing crop performance in a Canola hybrid is described, said method comprising:
a. providing Canola hybrid seeds which have been sorted so that at least 95% of the seed population have a seed diameter of at least 1.7 mm; and
b. seeding said Canola hybrid seeds at a seeding rate sufficient to establish a population of Canola hybrid plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

A method for enhancing crop performance in a Canola hybrid is described, said method comprising:
a. providing Canola hybrid seeds which have been sorted so that at least 90% of the seed population have a seed diameter of at least 1.7 mm; and
b. seeding said Canola hybrid seeds at a seeding depth of 1.9 to 3.2 cm and at a seeding rate sufficient to establish a population of Canola hybrid plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

A method for enhancing crop performance in a Canola hybrid is described, said method comprising:
a. providing Canola hybrid seeds which have been sorted so that at least 95% of the seed population have a seed diameter of at least 1.7 mm; and
b. seeding said Canola hybrid seeds at a seeding depth of 1.9 to 3.2 cm and at a seeding rate sufficient to establish a population of Canola hybrid plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

A method for enhancing crop performance in a Canola hybrid, said method comprising:
a. providing Canola hybrid seeds which have been sorted so that at least 95% of the seed population have a seed diameter of at least 1.7 mm; and
b. seeding said Canola hybrid seeds at a seeding depth of 1.9 to 3.2 cm and at a seeding rate sufficient to establish a population of Canola hybrid plants having the following characteristics:
1) a density of 40 to 95 plants per m² when the plants are at any one or more of phenological growth stages 11, 12, 13, 14, or 15, according to the BBCH scale; and
2) an establishment rate of at least 50%,
3) harvesting the resulting crop between BBCH stage 84 and 89 using the straight-cutting technique.

A method for enhancing crop performance in *Brassica napus* is described, said method comprising:
a. providing *Brassica napus* seeds which have been sorted so that the seed population has a TSW of more than 3.5 g, preferably 3.75 g; and
b. seeding said *Brassica napus* seeds at a seeding rate sufficient to establish a population of *Brassica napus* plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

A method for enhancing crop performance in *Brassica napus* is described, said method comprising:
a. providing *Brassica napus* seeds which have been sorted so that the seed population has a TSW of more than 3.5 g, preferably 3.75 g; and
b. seeding said *Brassica napus* seeds at a seeding depth of 1.9 to 3.2 cm and at a seeding rate sufficient to establish a population of *Brassica napus* plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

A method for enhancing crop performance in *Brassica napus*, said method comprising:
a. providing *Brassica napus* seeds which have been sorted so that the seed population has a TSW of more than 3.5 g, preferably 3.75 g; and
b. seeding said *Brassica napus* seeds at a seeding depth of 1.9 to 3.2 cm and at a seeding rate sufficient to establish a population of *Brassica napus* plants having the following characteristics:
1) a density of 40 to 95 plants per m² when the plants are at any one or more of phenological growth stages 11, 12, 13, 14, or 15, according to the BBCH scale; and
2) an establishment rate of at least 50%,
3) harvesting the resulting crop between BBCH stage 84 and 89 using the straight-cutting technique.

A method for enhancing crop performance in a Canola hybrid is described, said method comprising:
a. providing Canola hybrid seeds which have been sorted so that the seed population has a TSW of more than 3.5 g, preferably 3.75 g; and
b. seeding said Canola hybrid seeds at a seeding rate sufficient to establish a population of Canola hybrid plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

A method for enhancing crop performance in a Canola hybrid is described, said method comprising:
a. providing Canola hybrid seeds which have been sorted so that the seed population has a TSW of more than 3.5 g, preferably 3.75 g; and
b. seeding said Canola hybrid seeds at a seeding depth of 1.9 to 3.2 cm and at a seeding rate sufficient to establish a population of Canola hybrid plants having the following characteristics:
1) a density of 40 to 95 plants per m² when the plants are at any one or more of phenological growth stages 11, 12, 13, 14, or 15, according to the BBCH scale; and
2) an establishment rate of at least 50%.

A method for enhancing crop performance in a Canola hybrid, said method comprising:
a. providing Canola hybrid seeds which have been sorted so that the seed population has a TSW of more than 3.5 g, preferably 3.75 g; and
b. seeding said Canola hybrid seeds at a seeding depth of 1.9 to 3.2 cm and at a seeding rate sufficient to establish a population of Canola hybrid plants having the following characteristics:
1) a density of 40 to 95 plants per m² when the plants are at any one or more of phenological growth stages 11, 12, 13, 14, or 15, according to the BBCH scale; and
2) an establishment rate of at least 60%,
3) harvesting the resulting crop between BBCH stage 84 and 89 using the straight-cutting technique.

A method for enhancing crop performance in *Brassica napus* is described, said method comprising:
a. providing *Brassica napus* seeds which have been sorted so that at least 90% of the seed population have a seed diameter of at least 1.7 mm; and
b. seeding said *Brassica napus* seeds at a seeding rate sufficient to establish a population of *Brassica napus* plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%.

A method for enhancing crop performance in *Brassica napus* is described, said method comprising:
a. providing *Brassica napus* seeds which have been sorted so that at least 95% of the seed population have a seed diameter of at least 1.7 mm; and
b. seeding said *Brassica napus* seeds at a seeding rate sufficient to establish a population of *Brassica napus* plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%.

A method for enhancing crop performance in *Brassica napus* is described, said method comprising:
a. providing *Brassica napus* seeds which have been sorted so that at least 90% of the seed population have a seed diameter of at least 1.7 mm; and
b. seeding said *Brassica napus* seeds at a seeding depth of 1.9 to 3.2 cm and at a seeding rate sufficient to establish a population of *Brassica napus* plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%.

A method for enhancing crop performance in *Brassica napus* is described, said method comprising:
a. providing *Brassica napus* seeds which have been sorted so that at least 95% of the seed population have a seed diameter of at least 1.7 mm; and
b. seeding said *Brassica napus* seeds at a seeding depth of 1.9 to 3.2 cm and at a seeding rate sufficient to establish a population of *Brassica napus* plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%.

A method for enhancing crop performance in *Brassica napus*, said method comprising:
a. providing *Brassica napus* seeds which have been sorted so that at least 95% of the seed population have a seed diameter of at least 1.7 mm; and
b. seeding said *Brassica napus* seeds at a seeding depth of 1.9 to 3.2 cm and at a seeding rate sufficient to establish a population of *Brassica napus* plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%,
   3) harvesting the resulting crop between BBCH stage 84 and 89 using the straight-cutting technique.

A method for enhancing crop performance in a Canola hybrid is described, said method comprising:
a. providing Canola hybrid seeds which have been sorted so that at least 90% of the seed population have a seed diameter of at least 1.7 mm; and
b. seeding said Canola hybrid seeds at a seeding rate sufficient to establish a population of Canola hybrid plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%.

A method for enhancing crop performance in a Canola hybrid is described, said method comprising:
a. providing Canola hybrid seeds which have been sorted so that at least 95% of the seed population have a seed diameter of at least 1.7 mm; and
b. seeding said Canola hybrid seeds at a seeding rate sufficient to establish a population of Canola hybrid plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%.

A method for enhancing crop performance in a Canola hybrid is described, said method comprising:
a. providing Canola hybrid seeds which have been sorted so that at least 90% of the seed population have a seed diameter of at least 1.7 mm; and
b. seeding said Canola hybrid seeds at a seeding depth of 1.9 to 3.2 cm and at a seeding rate sufficient to establish a population of Canola hybrid plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%.

A method for enhancing crop performance in a Canola hybrid is described, said method comprising:
a. providing Canola hybrid seeds which have been sorted so that at least 95% of the seed population have a seed diameter of at least 1.7 mm; and
b. seeding said Canola hybrid seeds at a seeding depth of 1.9 to 3.2 cm and at a seeding rate sufficient to establish a population of Canola hybrid plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%.

A method for enhancing crop performance in a Canola hybrid, said method comprising:
a. providing Canola hybrid seeds which have been sorted so that at least 95% of the seed population have a seed diameter of at least 1.7 mm; and
b. seeding said Canola hybrid seeds at a seeding depth of 1.9 to 3.2 cm and at a seeding rate sufficient to establish a population of Canola hybrid plants having the following characteristics:
   1) a density of 40 to 95 plants per m$^2$ when the plants are at any one or more of phenological growth stages 11, 12, 13, 14, or 15, according to the BBCH scale; and
   2) an establishment rate of at least 60%,
   3) harvesting the resulting crop between BBCH stage 84 and 89 using the straight-cutting technique.

A method for enhancing crop performance in *Brassica napus* is described, said method comprising:

a. providing *Brassica napus* seeds which have been sorted so that the seed population has a TSW of more than 3.5 g, preferably 3.75 g; and b. seeding said *Brassica napus* seeds at a seeding rate sufficient to establish a population of *Brassica napus* plants having the following characteristics:
  1) a density of 40 to 95 plants per m² when the plants are at any one or more of phenological growth stages 11, 12, 13, 14, or 15, according to the BBCH scale; and
  2) an establishment rate of at least 60%.

A method for enhancing crop performance in *Brassica napus* is described, said method comprising:

a. providing *Brassica napus* seeds which have been sorted so that the seed population has a TSW of more than 3.5 g, preferably 3.75 g; and b. seeding said *Brassica napus* seeds at a seeding depth of 1.9 to 3.2 cm and at a seeding rate sufficient to establish a population of *Brassica napus* plants having the following characteristics:
  1) a density of 40 to 95 plants per m² when the plants are at any one or more of phenological growth stages 11, 12, 13, 14, or 15, according to the BBCH scale; and
  2) an establishment rate of at least 60%.

A method for enhancing crop performance in *Brassica napus*, said method comprising:

a. providing *Brassica napus* seeds which have been sorted so that the seed population has a TSW of more than 3.5 g, preferably 3.75 g; and b. seeding said *Brassica napus* seeds at a seeding depth of 1.9 to 3.2 cm and at a seeding rate sufficient to establish a population of *Brassica napus* plants having the following characteristics:
  1) a density of 40 to 95 plants per m² when the plants are at any one or more of phenological growth stages 11, 12, 13, 14, or 15, according to the BBCH scale; and
  2) an establishment rate of at least 60%,
  3) harvesting the resulting crop between BBCH stage 84 and 89 using the straight-cutting technique.

A method for enhancing crop performance in a Canola hybrid is described, said method comprising:

a. providing Canola hybrid seeds which have been sorted so that the seed population has a TSW of more than 3.5 g, preferably 3.75 g; and b. seeding said Canola hybrid seeds at a seeding rate sufficient to establish a population of Canola hybrid plants having the following characteristics:
  1) a density of 40 to 95 plants per m² when the plants are at any one or more of phenological growth stages 11, 12, 13, 14, or 15, according to the BBCH scale; and
  2) an establishment rate of at least 60%.

A method for enhancing crop performance in a Canola hybrid is described, said method comprising:

a. providing Canola hybrid seeds which have been sorted so that the seed population has a TSW of more than 3.5 g, preferably 3.75 g; and b. seeding said Canola hybrid seeds at a seeding depth of 1.9 to 3.2 cm and at a seeding rate sufficient to establish a population of Canola hybrid plants having the following characteristics:
  1) a density of 40 to 95 plants per m² when the plants are at any one or more of phenological growth stages 11, 12, 13, 14, or 15, according to the BBCH scale; and
  2) an establishment rate of at least 60%.

A method for enhancing crop performance in a Canola hybrid, said method comprising:

a. providing Canola hybrid seeds which have been sorted so that the seed population has a TSW of more than 3.5 g, preferably 3.75 g; and b. seeding said Canola hybrid seeds at a seeding depth of 1.9 to 3.2 cm and at a seeding rate sufficient to establish a population of Canola hybrid plants having the following characteristics:
  1) a density of 40 to 95 plants per m² when the plants are at any one or more of phenological growth stages 11, 12, 13, 14, or 15, according to the BBCH scale; and
  2) an establishment rate of at least 60%,
  3) harvesting the resulting crop between BBCH stage 84 and 89 using the straight-cutting technique.

The invention is further described without being limited in the following examples.

Example 1

Field Data

Canola seeds were fractionated into small, medium and large seeds using standard handsieves.

The following TSW were determined for four different varieties L252, L140P, L261 and 5440.

L252, L140P, L261 and 5440 are commercially available from Bayer CropScience Inc Canada within the Invigor brand lines and are registered as plant varieties under the Seeds Act Canada.

TABLE 1

| Variety | Fraction Name | TSW (g) | Seeding rate (kg/ha) |
|---|---|---|---|
| L252 | Small | 3.62 | 4.5 |
|  | Medium | 4.73 | 5.8 |
|  | Large | 6.54 | 8.0 |
| L140P | Small | 3.56 | 4.4 |
|  | Medium | 4.60 | 5.7 |
|  | Large | 6.28 | 7.7 |
| L261 | Small | 3.45 | 4.2 |
|  | Medium | 4.25 | 5.2 |
|  | Large | 5.70 | 7.0 |
| 5440 | Small | 3.70 | 4.6 |
|  | Medium | 4.85 | 6.0 |
|  | Large | 6.45 | 7.9 |

Three fractions denominated small, medium and large of Canola seeds of the four different variety L252, L140P, L261 and 5440 treated with Prosper Evergol (available from Bayer CropScience Inc), seed treatment comprising Clothianidin, Penflufen, Trifloxystrobin, Metalaxyl) were seeded using a standard cone plot seeder using Seed Hawk openers in 11 different locations of Alberta, Manitoba, and Saskatchewan between May 15$^{th}$ to June 5$^{th}$. The seeding rate was in average 123 seeds per square meter. All trials were treated during the season with herbicides one or two times in the two to six leaf stage (BBCH 12 to 16). All trials were sprayed with a commercial fungicide at the growth stage with thirty percent of flowers open (BBCH stage 63). The fields were harvested by swathing between August 15 and September 15$^{th}$ when a fifty percent color change in seeds was observed (app. BBCH stage 85).

The following plant densities were counted 21 days after seeding where the plants are in BBCH stage 13 to 14.

| | Plant density [plants/m$^2$] | | |
|---|---|---|---|
| Variety | Small | Medium | Large |
| 5440 | 73.7 | 85.0 | 86.6 |
| L140P | 84.3 | 91.7 | 91.3 |
| L252 | 81.4 | 91.1 | 89.8 |
| L261 | 81.2 | 90.0 | 91.7 |

The following yields were measured from the harvested crops.

TABLE 2

| Variety | Fraction Name | Yield [tons per ha] | Relative Yield compared to small fraction [%] |
|---|---|---|---|
| 5440 | Large | 2.89 | 108 |
| 5440 | Medium | 2.82 | 106 |
| 5440 | Small | 2.67 | 100 |
| L140P | Large | 3.00 | 103 |
| L140P | Medium | 3.00 | 103 |
| L140P | Small | 2.92 | 100 |
| L252 | Large | 2.94 | 104 |
| L252 | Medium | 2.96 | 105 |
| L252 | Small | 2.83 | 100 |
| L261 | Large | 2.88 | 106 |
| L261 | Medium | 2.86 | 105 |
| L261 | Small | 2.72 | 100 |

Example 2

Determination of Emergence, Fresh and Dry Weight and Average Shoot Length Under Laboratory Conditions Three replicates of two Canola varieties 5440 and L252 were sown into a peat/sand mix at a depth between 1.5 and 3 cm, exposing the seeds at a humidity of 50 to 75% to a 16 h photoperiod with 16 degree Celsius in the light and 5 degree Celsius in the dark and count the number of emerged seedlings until 14 days. The fresh weight, dry weight, and average shoot length were also determined as described above after 14 days.

The TSW was determined by weighing a thousand seeds and taking the average of 3 replicates. The seed size was determined using US standard seed sieves from Fisher Scientific.

Example 3

Field Data

Canola seeds were fractionated into small, medium, medium/large and large seeds using standard sieves. Unsized refers to the original, non fractionated, cleaned Canola seeds.

TSW were determined for five different varieties L130, L252, L140P, L261 and 5440.

L130, L252, L140P, L261 and 5440 are commercially available from Bayer CropScience Inc Canada within the Invigor brand lines and are registered as plant varieties under the Seeds Act Canada.

Five fractions denominated small, medium, medium/large and large and Unsized of Canola seeds of the four different variety L130, L252, L140P, L261 and 5440 treated with Prosper Evergol (available from Bayer CropScience Inc), seed treatment comprising Clothianidin, Penflufen, Trifloxystrobin, Metalaxyl) were seeded using a standard cone plot seeder using either Seed Hawk opener or John Deere 1870 Seeder in 27 different locations of Alberta, Manitoba, and Saskatchewan between April 28$^{th}$ to June 5$^{th}$. The seeding rate was 110 seeds per square meter for all trials. All trials were treated during the season with herbicides one or two times in the one to six leaf stage (BBCH 11 to 16). All trials were sprayed with a commercial fungicide at the growth stage with thirty percent of flowers open (BBCH stage 63). The fields were harvested by swathing between August 15$^{th}$ and September 15$^{th}$ when a fifty percent color change in seeds was observed (app. BBCH stage 85).

Plants stands were also determined by visual inspection of stubbles after harvest.

All trials conducted were randomized complete block design with four replicates with individual plots measuring 6.1 m by 37.5 m.

TABLE 3

| Variety | Fraction Size | TSW | Percentage of seeds ≤ 1.7 mm | Final emergence rate after 14 days [%] | fresh weight [g] | dry weight [g] | Average Shoot Length [cm] |
|---|---|---|---|---|---|---|---|
| 5440 | Unfractioned | 5.53 ± 0.88 | 6.47 ± 0.83 | 98.1 ± 1.1 | 18.38 ± 4.59 | 1.65 ± 0.40 | 6.05 ± 0.81 |
| 5440 | Small | 3.66 ± 0.02 | 19.43 ± 0.54 | 94.2 ± 3.1 | 16.38 ± 3.76 | 1.27 ± 0.21 | 6.29 ± 0.62 |
| 5440 | Medium | 4.46 ± 0.01 | 0.06 ± 0.03 | 97.7 ± 2.7 | 17.92 ± 1.57 | 1.52 ± 0.20 | 6.61 ± 0.28 |
| 5440 | Large | 5.50 ± 0.05 | 0.07 ± 0.07 | 97.7 ± 0.6 | 20.29 ± 3.39 | 1.65 ± 0.26 | 6.66 ± 0.87 |
| L252 | Unfractioned | 5.05 ± 0.05 | 7.98 ± 0.33 | 97.1 ± 0.6 | 24.75 ± 6.82 | 1.83 ± 0.48 | 6.04 ± 0.47 |
| L252 | Small | 3.38 ± 0.02 | 34.21 ± 1.55 | 94.7 ± 3.7 | 28.56 ± 5.64 | 2.00 ± 0.45 | 5.67 ± 0.28 |
| L252 | Medium | 4.60 ± 0.01 | 0.0 ± 0.0 | 98.2 ± 1.0 | 26.11 ± 8.28 | 2.12 ± 0.77 | 5.98 ± 0.62 |
| L252 | Large | 5.89 ± 0 | 0.0 ± 0.0 | 96.5 ± 1.8 | 37.42 ± 8.64 | 2.89 ± 0.61 | 7.23 ± 0.99 |

Hybrid L261

| Fraction | TSW (g) | Plant Count (days after seeding/BBCH) | | | | YIELD (T/Ha) |
|---|---|---|---|---|---|---|
| | | 15 days = BBCH 11 | 23 days = BBCH 14 | 30 days = BBCH 16 | after harvest = BBCH 100 | |
| Small | 3.23 | 48.8 | 43.2 | 40.2 | 40.8 | 2.83 |
| Medium | 4.15 | 51.7 | 47.2 | 41.7 | 47.2 | 2.85 |
| Med/Large | 4.45 | 54.2 | 48.6 | 42.5 | 45.1 | 2.93 |
| Large | 4.50 | 53.6 | 47.0 | 41.9 | 43.3 | 2.88 |
| Unsized | 4.14 | 52.2 | 47.1 | 42.0 | 42.2 | 2.91 |

Hybrid L140P

| Fraction | TSW (g) | Plant Count (days after seeding/BBCH) | | | | YIELD (T/Ha) |
|---|---|---|---|---|---|---|
| | | 15 days = BBCH 11 | 23 days = BBCH 14 | 30 days = BBCH 16 | after harvest = BBCH 100 | |
| Small | 2.87 | 52.0 | 49.1 | 45.6 | 48.1 | 2.89 |
| Medium | 4.23 | 56.8 | 51.4 | 49.5 | 50.1 | 2.95 |
| Med/Large | 4.30 | 56.6 | 52.3 | 49.9 | 50.1 | 2.94 |
| Large | 4.72 | 55.1 | 50.7 | 48.6 | 49.7 | 2.95 |
| Unsized | 4.35 | 54.0 | 49.7 | 48.8 | 50.7 | 2.96 |

Seed size for the small fraction was below 1.59 mm, for the medium fraction seed size was at least 1.79 mm, for the medium fraction at least 1.98 mm and for the large fraction at least 2.18 mm.

Hybrid L252

| Fraction | TSW (g) | Lot | Plant Count (days after seeding/BBCH) | | | | YIELD (T/Ha) |
|---|---|---|---|---|---|---|---|
| | | | 15 days = BBCH 11 | 23 days = BBCH 14 | 30 days = BBCH 16 | after harvest = BBCH 100 | |
| Small | 3.30 | A | 46.2 | 42.7 | 43.9 | 44.5 | 3.09 |
| Medium | 4.56 | A | 52.3 | 47.4 | 48.3 | 49.7 | 3.10 |
| Med/Lge | 4.85 | A | 52.7 | 50.2 | 50.0 | 52.6 | 3.15 |
| Large | 5.86 | A | 54.5 | 50.9 | 50.7 | 51.0 | 3.15 |
| Unsized | 5.08 | A | 52.7 | 50.8 | 48.5 | 50.4 | 3.12 |
| Small | 2.80 | B | 41.3 | 38.3 | 39.6 | 42.6 | 3.05 |
| Medium | 4.20 | B | 45.9 | 43.2 | 43.7 | 47.4 | 3.15 |
| Med/Lge | 4.64 | B | 47.5 | 46.2 | 46.4 | 45.5 | 3.16 |
| Large | 4.54 | B | 48.6 | 45.7 | 45.7 | 46.4 | 3.17 |
| Unsized | 3.28 | B | 40.8 | 38.4 | 39.2 | 41.8 | 3.16 |

Hybrid L130

| Fraction | TSW (g) | Plant Count (days after seeding/BBCH) | | | | YIELD (T/Ha) |
|---|---|---|---|---|---|---|
| | | 15 days = BBCH 11 | 23 days = BBCH 14 | 30 days = BBCH 16 | after harvest = BBCH 100 | |
| Small | 2.63 | 45.5 | 48.5 | 49.0 | 51.2 | 2.91 |
| Medium | 4.27 | 59.3 | 61.4 | 59.7 | 64.4 | 2.98 |
| Med/Large | 4.38 | 60.5 | 64.1 | 63.3 | 61.5 | 3.02 |
| Large | 4.47 | 56.6 | 58.0 | 57.2 | 60.5 | 3.02 |
| Unsized | 3.97 | 53.0 | 55.4 | 54.1 | 57.1 | 3.06 |

Hybrid 5440

|  |  |  | Plant Count (days after seeding/BBCH) | | | | |
| --- | --- | --- | --- | --- | --- | --- | --- |
| Fraction | TSW (g) | Lot | 15 days = BBCH 11 | 23 days = BBCH 14 | 30 days = BBCH 16 | after harvest = BBCH 100 | YIELD (T/Ha) |
| Small | 2.84 | A | 44.6 | 41.7 | 39.6 | 43.6 | 2.86 |
| Medium | 4.47 | A | 50.5 | 47.9 | 45.8 | 47.4 | 2.93 |
| Med/Lge | 4.94 | A | 49.7 | 47.9 | 44.6 | 47.9 | 2.94 |
| Large | 5.52 | A | 49.3 | 46.0 | 43.1 | 45.3 | 2.92 |
| Unsized | 4.52 | A | 48.3 | 47.2 | 43.3 | 45.4 | 2.93 |
| Small | 3.58 | B | 45.0 | 43.1 | 39.7 | 41.0 | 2.81 |
| Medium | 4.71 | B | 47.0 | 45.2 | 42.8 | 44.6 | 2.85 |
| Med/Lge | 5.98 | B | 49.6 | 47.7 | 44.0 | 46.3 | 2.90 |
| Large | 6.14 | B | 51.4 | 49.4 | 46.0 | 46.9 | 2.95 |
| Unsized | 5.20 | B | 49.5 | 45.2 | 42.6 | 46.6 | 2.93 |

Example 4

Biomass gain and the development of canola seedlings was analyzed in greenhouse for small and large seed fraction of L252 and 5440 Canola hybrids 14 days after seeding.

| Hybrid | Seed fraction | Average shoot length | Fresh weight (g) | Dry weight (g) |
| --- | --- | --- | --- | --- |
| L252 | S | 5.67 +/− 0.28 | 28.56 +/− 5.64 | 2.00 +/− 0.45 |
| L252 | L | 7.23 +/− 0.99 | 37.42 +/− 8.64 | 2.89 +/− 0.61 |
| 5440 | S | 6.29 +/− 0.62 | 16.38 +/− 3.76 | 1.27 +/− 0.21 |
| 5440 | L | 6.66 +/− 0.87 | 20.29 +/− 3.39 | 1.65 +/− 0.26 |

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the scope of the appended claims.

The invention claimed is:

1. A method for enhancing crop performance in *Brassica*, said method comprising:
   a. providing Brassica seeds which have been sorted so that the seed population has a thousand seed weight of more than 4.0 g;
   b. seeding said *Brassica* seeds at a seeding rate between 2.6 and 8.0 kg/ha; and
   c. growing the plants at
      a density of 40 to 95 plants per $m^2$ when the plants are at any one or more of phenological growth stages 11, 12, 13, 14, or 15, according to the BBCH scale, wherein the establishment rate of said seeds is at least 40%.

2. The method according to claim 1, wherein the seeding rate for the *Brassica* seeds is between 2.6 and 6.0 kg/ha.

3. The method according to claim 1, wherein the crop performance comprises a yield of at least 103% of the yield of an unbiased seed lot.

4. The method according to claim 1, wherein the resulting *Brassica* plants are harvested by the straight-cutting technique between BBCH stage 84 and 89.

5. The method according to claim 1, wherein the *Brassica* is *Brassica napus*.

6. The method according to claim 1, wherein the *Brassica* is spring oilseed rape.

7. The method according to claim 1, wherein the *Brassica* is a Canola variety.

8. The method according to claim 1, wherein the *Brassica* is a Canola hybrid.

9. The method according to claim 1, wherein the *Brassica* is a Canola hybrid which is resistant to glyphosate.

10. The method according to claim 1, wherein the *Brassica* is a Canola hybrid which is resistant to glufosinate.

11. The method according to claim 1, wherein the *Brassica* is a Canola hybrid which is resistant to an herbicide being an inhibitor of acetolactate synthase.

12. The method according to claim 1, wherein the *Brassica* is a Canola hybrid which is resistant to an herbicide selected from the group 3,6-dichloro-2-methoxybenzoic acid (dicamba), and 2,4-dichlorophenoxyacetic acid.

* * * * *